United States Patent [19]

Saari

[11] 4,442,103

[45] Apr. 10, 1984

[54] TREATING SEDATION WITH 1-(3-SUBSTITUTED-2-PYRIDINYL) PIPERAZINES

[75] Inventor: Walfred S. Saari, Lansdale, Pa.

[73] Assignee: Merck & Co., Inc., Rahway, N.J.

[21] Appl. No.: 430,914

[22] Filed: Sep. 30, 1982

Related U.S. Application Data

[63] Continuation-in-part of Ser. No. 267,326, May 26, 1981, abandoned.

[51] Int. Cl.$^3$ .......................................... A61K 31/495
[52] U.S. Cl. ..................................... 424/250; 544/360
[58] Field of Search .......................................... 424/250

[56] References Cited

U.S. PATENT DOCUMENTS

| | | | |
|---|---|---|---|
| 2,958,694 | 11/1960 | Jannsen | 544/360 |
| 3,773,951 | 11/1973 | Rodriguez | 424/250 |
| 4,078,063 | 3/1978 | Lumma et al. | 424/250 |
| 4,081,542 | 4/1978 | Lumma et al. | 424/250 |
| 4,082,844 | 4/1978 | Lumma et al. | 424/250 |
| 4,310,524 | 1/1982 | Wiech et al. | 424/244 |

OTHER PUBLICATIONS

Thunus; L. et al., *Ann. Pharm. Fran.*, 32, 569–574 (1974).

*Primary Examiner*—Richard A. Schwartz
*Attorney, Agent, or Firm*—William H. Nicholson; Mario A. Monaco

[57] ABSTRACT

1-(3-Substituted-2-pyridinyl)piperazines and their acid addition salts are selective $\alpha_2$-adrenergic receptor antagonists and thereby useful as antidepressant agents and for treating sedation caused by antihypertensive therapy.

4 Claims, No Drawings

TREATING SEDATION WITH 1-(3-SUBSTITUTED-2-PYRIDINYL) PIPERAZINES

BACKGROUND OF THE INVENTION

This is a continuation-in-part of application, Ser. No. 267,326, filed May 26, 1981 now abandoned.

This invention is concerned with a novel method of treating depression or antihypertensive agent-induced sedation by the administration of 1-(3-substituted-2-pyridinyl)piperazines which are selective $\alpha_2$-adrenergic receptor antagonists.

The piperazinyl group is particularly ubiquitous among compounds with useful pharmacological properties. Piperazinylpyrazines (U.S. Pat. Nos. 4,081,542 and 4,082,844), piperazinylquinoxalines (French patent publication No. 2,236,499) and 2-piperazinyl-5 (and/or 6)-substituted pyridines (U.S. Pat. No. 4,078,063) are known anorexigenic agents which are also said to have antidepressant activity by virtue of their pharmacological influence on serotonin levels.

Now, with the present invention there is provided a novel method of treating depression and antihypertensive agent-induced sedation by the administration of 1-(3-substituted-2-pyridinyl)piperazines which are $\alpha_2$-adrenergic receptor antagonists.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters. Combinations of norepinephrine reuptake blockers with selective $\alpha_2$-adrenergic receptor antagonists, their effects being at least additive, form another aspect of this invention.

In addition to $\alpha_1$-adrenergic receptors which mediate postsynaptic responses to the neurotransmitter, norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norephinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

Mianserin, a clinically effective antidepressant which has been reported to have minimal in vivo norepinephrine reuptake inhibiting properties, blocks $\alpha_2$-adrenergic receptors. However, mianserin fails to exhibit any important selectivity for $\alpha_1$- or $\alpha_2$-adrenergic receptors suggesting that mianserin, in vivo, blocks $\alpha_1$-receptors at about the same dose required to block $\alpha_2$-receptors (Clineschmidt et al., *Arch. Int. Pharmacodyn. Ther.*, 242 59 (1979)).

The compounds of the present invention, being highly selective for the $\alpha_2$-adrenergic receptor, have definite therapeutic advantages over the more non-selective $\alpha_1$-, $\alpha_2$-antagonists. Since $\alpha_1$- (or post-synaptic) blockade opposes the increase in nor-adrenergic transmission initiated through $\alpha_2$-blockade, compounds that selectively antagonize $\alpha_2$-adrenergic receptors induce enhanced neurotransmission at nor-adrenergic synapses. In addition, molecules with reduced $\alpha_1$-receptor blocking properties, such as the compounds of the present invention, produce less orthostatic hypotension, and undesirable side-effect (Synder, *Pharmakopsychiat*, 13, 62 (1980)).

Sedation, the limiting side effect produced by some antihypertensive agents, is believed to be associated with stimulation of presynaptic $\alpha_2$-adrenergic receptors. However, the lowering of blood pressure is not related to these receptors, but rather to postsynaptic adrenergic receptors (Birch et al., *Br. J. Pharmacol.*, 68, 107P (1979)). Selective $\alpha_2$-receptor antagonists should be useful in reducing the adverse effect of sedation produced by some antihypertensive drugs. Thus, the selective $\alpha_2$-receptor blocker, yohimbine, antagonizes the sedation produced by clonidine (Drew et al., *Br. J. Pharmacol.*, 67, 133 (1979)) and the locomotor depressant effects of methyldopa in rats (Clineschmidt et al., *Arch. Int. Pharmacodyn. Ther.*, 244, 231 (1980)). In addition, yohimbine has been reported to reduce clonidine-induced sedation in man (Autret et al., *Eur. J. Clin. Pharmacol.*, 12, 319 (1977)).

The compounds useful in the novel method of treatment of the present invention, being highly selective for the $\alpha_2$-adrenergic receptor, effectively reduce the sedative effects of antihypertensive agents without affecting the blood pressure lowering properties. Combinations of antihypertensive agents with selective $\alpha_2$-adrenergic receptor antagonists form an additional aspect of this invention.

DETAILED DESCRIPTION OF THE INVENTION

This invention is concerned with the use of a compound to selectively antagonize $\alpha_2$-adrenergic receptors wherein the compound is of structural formula:

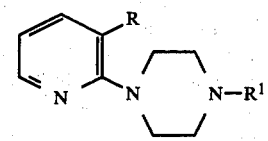

or a pharmaceutically acceptable salt thereof, wherein:
R is
(1) hydrogen;
(2) halo, such as chloro, bromo, iodo or fluoro, especially fluoro or chloro;
(3) $C_{1-4}$ alkyl, especially methyl;
(4) cyano;
(5) $C_{1-4}$ alkoxy, especially methoxy;
(6) trifluoromethyl; or
(7) nitro; and
$R^1$ is
(1) hydrogen, or
(2) $C_{1-3}$ alkyl;
preferably hydrogen; with the proviso, that if R is fluoro, chloro, or bromo, then $R^1$ is $C_{1-3}$ alkyl.

The pharmaceutically acceptable salts coming within the purview of this invention include the pharmaceutically acceptable acid-addition salts. Acids useful for preparing these acid-addition salts include inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The compounds useful in the novel method of treatment of the present invention are prepared by reaction of 2-X-3-R-pyridines of formula I with piperazines of formula II, as shown in Reaction Scheme I.

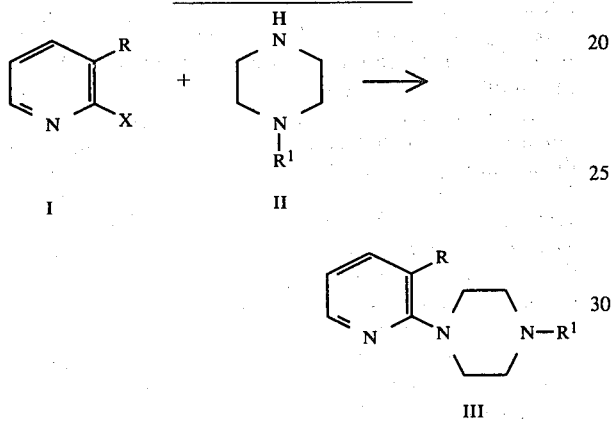

X is halogen, especially chloro, $C_{1-5}$alkylsulfonyloxy, such as methanesulfonyloxy; or arylsulfonyloxy such as, benzenesulfonyloxy or toluenesulfonyloxy.

The reaction takes place at temperatures ranging from about ambient to about 200° C., preferably under an inert atmosphere, e.g., $N_2$, He or Ar, until a substantial amount of desired compound of formula III is obtained, typically for a period of from about 0.25 to about 5 days, preferably from about 0.5 to about 3 days.

The reaction may be conducted neat, in the absence of solvent or in an inert organic solvent such as a $C_{2-5}$ alkanol, preferably butanol, acetonitrile, dimethylformamide, or dimethylsulfoxide.

In the novel method of selectively antagonizing $\alpha_2$-adrenergic receptors in a patient, an active compound or pharmaceutically acceptable salt thereof is administered in an amount ranging from about 0.01 to about 20 mg per kg of body weight per day, preferably from about 0.1 to about 10 mg per kg of body weight per day in a single dose or in 2 to 4 divided doses.

These doses are useful for treating depression or for treating sedation caused by antihypertensive chemotherapy.

If used in combination with a norepinephrine reuptake-blocker antidepressant, the dose of each is about half the recommended dose.

The compounds, or pharmaceutically acceptable salts thereof, of the present invention, in the described dosages, are administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples illustrate the preparation of compounds active in the present invention.

EXAMPLE 1

1-(3-Fluoro-2-Pyridinyl)Piperazine Dihydrochloride

A solution of 2-chloro-3-fluoropyridine (500 mg, 4.25 mmol) and anhydrous piperazine (3.66 g, 42.5 mmol) in 40 ml of n-butanol is stirred at reflux for 18 hours. After concentrating to dryness in vacuo, the residue is partitioned between toluene and dilute sodium hydroxide solution (5% w/v). The toluene layer is washed with a saturated sodium chloride solution, dried over $Na_2SO_4$, filtered and concentrated to 0.65 g of oil. Upon treatment of the oil with ethanolic hydrogen chloride and crystallization by dissolving the crude material in a minimum of methanol:ethanol (1:1) mixture and addition of ethyl acetate to incipient cloudiness, there is obtained 0.38 g., (35% yield) of product, m.p. 203°–210° C.

Calculated for $C_9H_{12}FN_3·2HCl$: C, 42.53; H, 5.55; N, 16.53. Found: C, 42.16; H, 5.64; N, 16.39.

EXAMPLE 2

1-(3-Iodo-2-pyridinyl)piperazine Dihydrochloride

A solution of 2-chloro-3-iodopyridine (2.39 g, 10 mmol) and piperazine (8.61 g, 100 mmol) in n-BuOH, 100 mL, was stirred at reflux under $N_2$ for 18 h. After removing most of the n-BuOH under reduced pressure, the residue was partitioned between toluene and 10% NaOH. The toluene layer was washed further with water, dried ($Na_2SO_4$), filtered and concentrated to an oil. The pyridinylpiperazine was purified by recrystallization of the dihydrochloride salt from methanol-ethanol-ethylacetate, m.p. 185°–189° C. (dec.).

EXAMPLE 3

1-(3-Nitro-2-pyridinyl)piperazine

A solution of 2-chloro-3-nitropyridine (4.76 g, 30 mmol) and piperazine (5.9, 69 mmol) in acetonitrile, (75 mL), was stirred at reflux for 5 h. After concentrating under reduced pressure, the residue was partitioned between ethyl acetate and 10% NaOH. The ethyl acetate extract was washed with water, dried ($Na_2SO_4$), filtered and concentrated. Flash chromatography over $Al_2O_3$ and elution with 2% MeOH-98% $CHCl_3$ afforded the title compound, m.p. 82°–87° C. An analytical sample, m.p. 83.5°–86.5° C., was obtained upon recrystallization from $CHCl_3$-hexane.

Following the procedure substantially as described in Example 1 or 2, but substituting for the starting materials used therein, an equimolar amount of the 2-X-3-R-pyridines described in Table I, there are produced the corresponding 1-(3-R-2-pyridinyl)-piperazines also described in Table I, in accordance with reaction scheme I.

TABLE I

| Method of Example | X | R | R1 | m.p. (° C.) |
|---|---|---|---|---|
| 1 | Cl | Br | H | 180 (dec.) (HC.½ H₂O) |
| 1 | Cl | Cl | H | 142–144 (HCl) |
| 2 | Cl | CN | H | 210–218 (dec.) (2HCl) |
| 2 | Cl | CF₃ | H | 174–178 (HCl) |
| 1 | Cl | F | CH₃ | 148–149 (C₄H₄O₄) |

TABLE I-continued

| Method of Example | X | R | R1 | m.p. (° C.) |
|---|---|---|---|---|
| 1 | Cl | Cl | $CH_3$ | 203-205 (HCl) |
| 1 | Cl | Br | $CH_3$ | 210-212 (dec.) (HCl) |

EXAMPLE 4

Adrenergic Receptor Binding Assays for 1-(3-R-2-pyridinyl)piperazines and Related Compounds The $\alpha_1$- and $\alpha_2$-adrenergic receptor binding was determined for 1-(3-R-2-pyridinyl)-piperazines and is shown in Table II.

Extent of binding to the $\alpha_1$-adrenergic receptor was determined by the method of Greengrass and Bremner, *Eur. J. Pharmacol.*, 55, 323 (1979) and is expressed in Table II as Ki, representing the affinity of each compound for the [$^3$H] prazosin binding site in calf cerebral cortex.

Binding to the $\alpha_2$-adrenergic receptor was determined by the method of Lyon and Randall, *Life Sciences*, 26, 1121 (1980) and also is expressed in Table II as Ki representing the affinity of each compound for the [$^3$H] clonidine binding site in calf cerebral cortex.

TABLE II

Adrenergic Receptor Binding of 1-(3-R—2-pyridinyl)-piperazine and Related Compounds

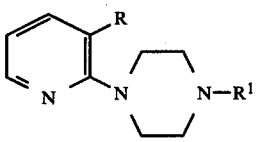

| | | | Adrenergic Binding Ki(nM) | | |
|---|---|---|---|---|---|
| Compound | R | $R^1$ | $\alpha_2$ | $\alpha_1$ | $\alpha_1/\alpha_2$ |
| 1 | 3-I | H | 42 | 1600 | 38 |
| 2[a] | 3-Br | —$CH_3$ | 2.9 | 160 | 55 |
| 3 | 3-$CF_3$ | H | 97 | 2850 | 29 |
| 4[b] | H | H | 37 | 2400 | 65 |
| 5 | $NO_2$ | H | 26 | 3800 | 146 |
| 6 | F | $CH_3$ | 5 | 490 | 98 |
| 7 | Cl | $CH_3$ | 2.7 | 215 | 7 |

[a] Ann. Pharm. franc., 32, 569 (1974).
[b] U.S. Pat. No. 3,733,951.

Clearly the compounds of the novel method of treatment of this invention have strong affinity (low Ki), for the $\alpha_2$-adrenergic receptors and weak affinity (high Ki) for the $\alpha_1$-adrenergic receptors. Accordingly they have great selectivity or ratio of $Ki_\alpha/Ki_\alpha$.

EXAMPLE 5

Pharmaceutical Formulation

| Inqredient | Mg/Capsule |
|---|---|
| 1-(3-nitro-2-pyridinyl) pyrazine dihydrochloride | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 6

Pharmaceutical Formulation—including a norepinephrine reuptake blocker

| Ingredients | Mg/capsule |
|---|---|
| 1-(3-fluoro-2-pyridinyl) pyrazine dihydrochloride | 3 |
| amitriptyline hydrochloride | 15 |
| starch | 75 |
| magnesium stearate | 7 |

The active ingredient, starch and magnesium stearate are blended together. The mixture is used to fill hard shell capsules of a suitable size at a fill weight of 100 mg per capsule.

EXAMPLE 7

Pharmaceutical Formulation including an antihypertensive agent

| Ingredients | Mg/capsule |
|---|---|
| 1-(3-fluoro-2-pyridinyl) pyrazine dihydrochloride | 6 |
| methyldopa | 250 |
| starch | 219 |
| magnesium stearate | 25 |

The active ingredient, starch and magnesium stearate are blended together. The mixture is used to fill hard shell capsules of a suitable size at a fill weight of 500 mg per capsule.

What is claimed is:

1. A method of treating sedation caused by presynaptic $\alpha_2$-adrenergic receptor stimulation by antihypertensive drug therapy in a patient in need of such treatment which comprises the administration of 0.01 to 20 mg/kg/day of a compound of structural formula:

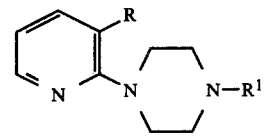

or a pharmaceutically acceptable salt thereof, wherein:
R is
 (1) hydrogen;
 (2) halo;
 (3) $C_{1-4}$alkyl;
 (4) cyano;
 (5) $C_{1-4}$alkoxy;
 (6) trifluoromethyl; or
 (7) nitro; and
$R^1$ is
 (1) hydrogen, or
 (2) $C_{1-3}$alkyl;
with the proviso that if R is fluoro, chloro or bromo, $R^1$ is $C_{1-3}$alkyl.

2. The method of claim 1, wherein R is hydrogen, halo, methyl, cyano, nitro or trifluoromethyl; and $R^1$ is hydrogen or methyl.

3. A pharmaceutical composition for treating sedation caused by presynaptic $\alpha_2$-adrenergic receptor stimulation by antihypertensive drug therapy which comprises a pharmaceutical carrier, an effective amount of a presynaptic α₂-adrenergic receptor stimulating antihypertensive agent and an effective amount of a compound of structural formula:

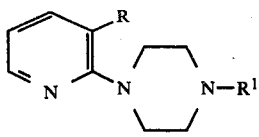

or a pharmaceutically acceptable salt thereof, wherein:
R is
(1) hydrogen;
(2) halo;
(3) C₁₋₄alkyl;
(4) cyano;
(5) C₁₋₄alkoxy;
(6) trifluoromethyl; or
(7) nitro; and
R¹ is
(1) hydrogen, or
(2) C₁₋₃alkyl;
with the proviso that if R is fluoro, chloro or bromo, R¹ is C₁₋₃alkyl.

4. The composition of claim 3, wherein R is hydrogen, halo, methyl, cyano, nitro or trifluoromethyl; and R¹ is hydrogen or methyl.

* * * * *